United States Patent
Ho et al.

(10) Patent No.: US 10,589,271 B2
(45) Date of Patent: Mar. 17, 2020

(54) BLOOD PLASMA AND BLOOD CELL SEPARATION DEVICE AND SEPARATING METHOD THEREOF

(71) Applicant: SKYLA CORPORATION HSINCHU SCIENCE PARK BRANCH, Hsinchu (TW)

(72) Inventors: Ping-Hsing Ho, Taipei (TW); Chia-Chun Wei, Taipei (TW); Hung-Wei Chen, Taipei (TW)

(73) Assignee: SKYLA CORPORATION HSINCHU SCIENCE PARK BRANCH, Hsinchu (TW)

( * ) Notice: Subject to any disclaimer, the term of this patent is extended or adjusted under 35 U.S.C. 154(b) by 387 days.

(21) Appl. No.: 15/647,273

(22) Filed: Jul. 12, 2017

(65) Prior Publication Data

US 2018/0304261 A1 Oct. 25, 2018

(30) Foreign Application Priority Data

Apr. 24, 2017 (CN) .......................... 2017 1 0270473

(51) Int. Cl.
*B01L 3/00* (2006.01)
*B01D 39/00* (2006.01)
(Continued)

(52) U.S. Cl.
CPC ........ *B01L 3/502753* (2013.01); *B01D 39/00* (2013.01); *B01D 61/147* (2013.01);
(Continued)

(58) Field of Classification Search
CPC .. A61M 1/029; A61M 1/3693; A61M 1/3696; B01L 3/5023; B01L 3/202753;
(Continued)

(56) References Cited

U.S. PATENT DOCUMENTS

| 2012/0024788 A1* | 2/2012 | Kelso .................... B01L 3/5023 210/651 |
| 2016/0029936 A1 | 2/2016 | Kvam et al. |
| 2016/0274010 A1 | 9/2016 | Ichiki et al. |

FOREIGN PATENT DOCUMENTS

| CN | 103229053 | 6/2015 |
| WO | 2012103511 | 8/2012 |

(Continued)

OTHER PUBLICATIONS

"Office Action of Taiwan Counterpart Application", dated Aug. 21, 2018, p. 1-p. 7.

(Continued)

*Primary Examiner* — Philip R Wiest
(74) *Attorney, Agent, or Firm* — JCIPRNET (57) ABSTRACT

A blood plasma and blood cell separation device includes a first body, a blood plasma separation membrane and a second body. The first body has an injection port. The blood plasma separation membrane is disposed on the first body. The second body is movably assembled to the first body and has a collecting stage. The collecting stage has a collecting surface and a sampling recess on the collecting stage. When a blood enters the blood plasma separation membrane from the injection port of the first body, a blood plasma in the blood plasma separation membrane is separated by a capillary force between the collecting stage of the second body and the blood plasma separation membrane, and the blood plasma enters in the sampling recess by a relative movement between the first body and the second body.

10 Claims, 6 Drawing Sheets

(51) Int. Cl.
    *G01N 33/49*     (2006.01)
    *B01D 63/08*     (2006.01)
    *B01D 61/14*     (2006.01)
    *B01D 61/18*     (2006.01)
    *A61B 5/145*     (2006.01)

(52) U.S. Cl.
    CPC ........... B01D 61/18 (2013.01); B01D 63/087 (2013.01); B01L 3/502 (2013.01); G01N 33/491 (2013.01); *A61B 5/14* (2013.01); *B01L 2200/028* (2013.01); *B01L 2200/0668* (2013.01); *B01L 2300/0681* (2013.01); *B01L 2400/0406* (2013.01); *B01L 2400/0457* (2013.01)

(58) Field of Classification Search
    CPC .. B01L 39/00; B01L 2300/0681; B01L 3/502; B01L 3/502753; B01L 2300/068; A61B 5/14; B01D 61/147; B01D 61/18; B01D 63/087

See application file for complete search history.

(56) References Cited

FOREIGN PATENT DOCUMENTS

| | | |
|---|---|---|
| WO | 2016073415 | 5/2016 |
| WO | 2017015243 | 1/2017 |

OTHER PUBLICATIONS

"Office Action of China Counterpart Application", dated Aug. 21, 2018, p. 1-p. 7.
"Search Report of Europe Counterpart Application", dated Mar. 18, 2018, p. 1-p. 5, in which the listed references were cited.

* cited by examiner

BLOOD PLASMA AND BLOOD CELL SEPARATION DEVICE AND SEPARATING METHOD THEREOF

CROSS REFERENCE TO RELATED APPLICATION

This application claims the priority benefit of China application serial no. 201710270473.7, filed on Apr. 24, 2017. The entirety of the above-mentioned patent application is hereby incorporated by reference herein and made a part of specification.

BACKGROUND OF THE INVENTION

Field of the Invention

The invention relates to a separation device and a separating method, and particularly relates to a blood plasma and blood cell separation device and a separating method thereof.

Description of Related Art

When blood plasma is used to perform an immune test, it is generally necessary to collect venous blood first and then use a blood plasma centrifuge for separating blood plasma and blood cell. Since the blood plasma centrifuge is more expensive and occupies more space, it is not suitable to be used in the pharmacy system and for home care. To facilitate blood plasma and blood cell separation, a product using a blood plasma separation membrane to separate the blood plasma has already existed in the current market, which has the design of pores in the blood plasma separation membrane to filter out the blood plasma in the blood. In such kind of product that uses the blood plasma separation membrane to separate the blood plasma, since the filtered blood plasma will be stored in the blood plasma separation membrane, it is generally necessary to utilize an additional absorbent material to absorb the blood plasma in the blood plasma separation membrane and then collect the blood plasma by squeezing the absorbent material. However, since the foregoing method requires more steps, the required operation time becomes longer. Moreover, since the blood plasma, besides passing through the blood plasma separation membrane, is required to be absorbed by the absorbent material, and since the blood plasma cannot be completely extruded during the process of squeezing the absorbent material, the blood plasma separated from the blood by the foregoing method has a lower utilization rate. Besides, since it is necessary to use the absorbent material, the cost of the consumables required by the foregoing method is also higher.

SUMMARY OF THE INVENTION

The invention provides a blood plasma and blood cell separation device that obtains the desired sample of blood plasma in an effective and speedy manner.

The invention further provides a blood plasma and blood cell separating method that allows a user to obtain the desired sample of blood plasma in a short time with only a small amount of whole blood.

The blood plasma and blood cell separation device of the invention includes a first body, a blood plasma separation membrane, and a second body. The first body has an injection port. The blood plasma separation membrane is disposed on the first body. The second body is movably assembled to the first body and has a collecting stage. The collecting stage has a collecting surface and a sampling recess on the collecting stage. When a blood enters the blood plasma separation membrane from the injection port of the first body, a blood plasma in the blood plasma separation membrane is separated by a capillary force between the collecting stage of the second body and the blood plasma separation membrane, and the blood plasma enters in the sampling recess by a relative movement between the first body and the second body.

In an embodiment of the invention, the first body has a first surface facing the second body, and the first surface is provided with a membrane carrier protruding toward the second body. The injection port is disposed on the membrane carrier, and the blood plasma separation membrane is fixed on the membrane carrier.

In an embodiment of the invention, when the blood plasma separation membrane and the collecting stage are in a first relative position, the blood plasma separation membrane and the collecting surface has a first overlapping surface. When the blood plasma separation membrane and the collecting stage are in a second relative position, the blood plasma separation membrane and the collecting surface has a second overlapping surface. An area of the second overlapping surface is smaller than an area of the first overlapping surface.

In an embodiment of the invention, the second body has a second surface facing the first body, the collecting stage protrudes from the second surface toward the first body, and the sampling recess is recessed from the collecting surface.

In an embodiment of the invention, the first body has a first connecting portion, and the second body has a second connecting portion movably and detachably connected to the first connecting portion.

The blood plasma and blood cell separating method of the invention is adapted for a blood plasma and blood cell separation device. The blood plasma and blood cell separation device includes a first body, a blood plasma separation membrane, and a second body. The first body has an injection port, the blood plasma separation membrane is disposed on the first body, and the second body is movably assembled to the first body. The second body has a collecting stage that has a collecting surface and a sampling recess on the collecting stage. The blood plasma and blood cell separating method includes the following steps: injecting a blood into the injection port of the first body so that the blood plasma separation membrane absorbs the blood from the injection port; separating a blood plasma in the blood plasma separation membrane by a capillary force between the collecting stage of the second body and the blood plasma separation membrane; and generating a relative movement between the first body and the second body so that the blood plasma enters in the sampling recess.

In an embodiment of the invention, the first body has a first surface facing the second body, and the first surface is provided with a membrane carrier protruding toward the second body. The injection port is disposed on the membrane carrier, and the blood plasma separation membrane is fixed on the membrane carrier.

In an embodiment of the invention, when the blood plasma separation membrane and the collecting stage are in a first relative position, the blood plasma separation membrane and the collecting surface has a first overlapping surface. When the blood plasma separation membrane and the collecting stage are in a second relative position, the blood plasma separation membrane and the collecting surface has a second overlapping surface. An area of the second overlapping surface is smaller than an area of the first overlapping surface.

In an embodiment of the invention, the second body has a second surface facing the first body, the collecting stage protrudes from the second surface toward the first body, and the sampling recess is recessed from the collecting surface.

In an embodiment of the invention, the first body has a first connecting portion, and the second body has a second connecting portion movably and detachably connected to the first connecting portion.

Based on the above, in the design of the blood plasma and blood cell separation device of the invention, the blood plasma in the blood plasma separation membrane is separated by a capillary force between the collecting stage of the second body and the blood plasma separation membrane, and the blood plasma enters in the sampling recess by the relative movement between the first body and the second body. In this way, the user simply needs to disassemble the first body and the second body to obtain the desired sample of the blood plasma. In other words, the blood plasma and blood cell separation device of the invention obtains the desired sample of the blood plasma in an effective and speedy manner, while the blood plasma and blood cell separating method using the blood plasma and blood cell separation device of the invention allows the user to obtain the desired sample of the blood plasma in a short time with only a small amount of whole blood.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1A:
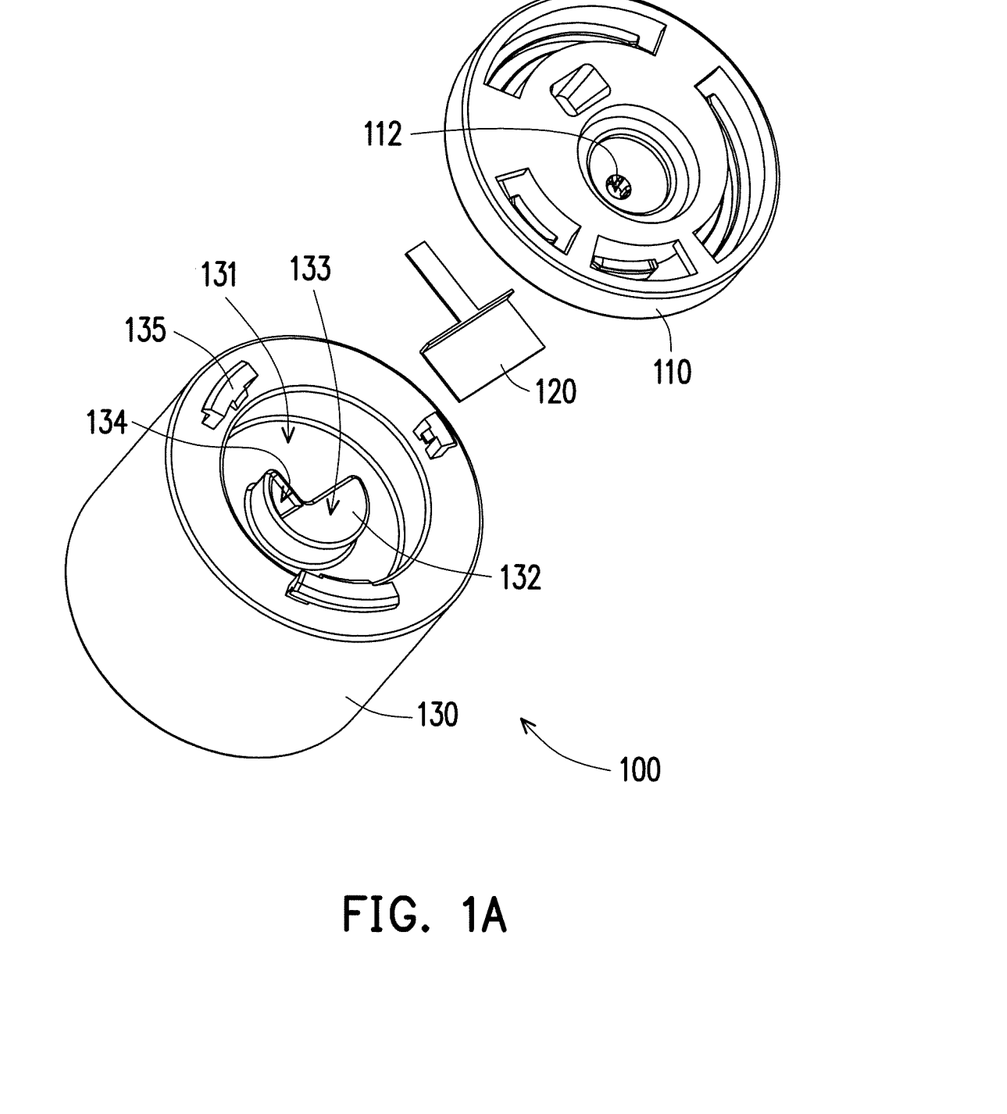
FIG. 1A shows a schematic three-dimensional exploded view of a blood plasma and blood cell separation device in an embodiment of the invention.
Figure 1B:
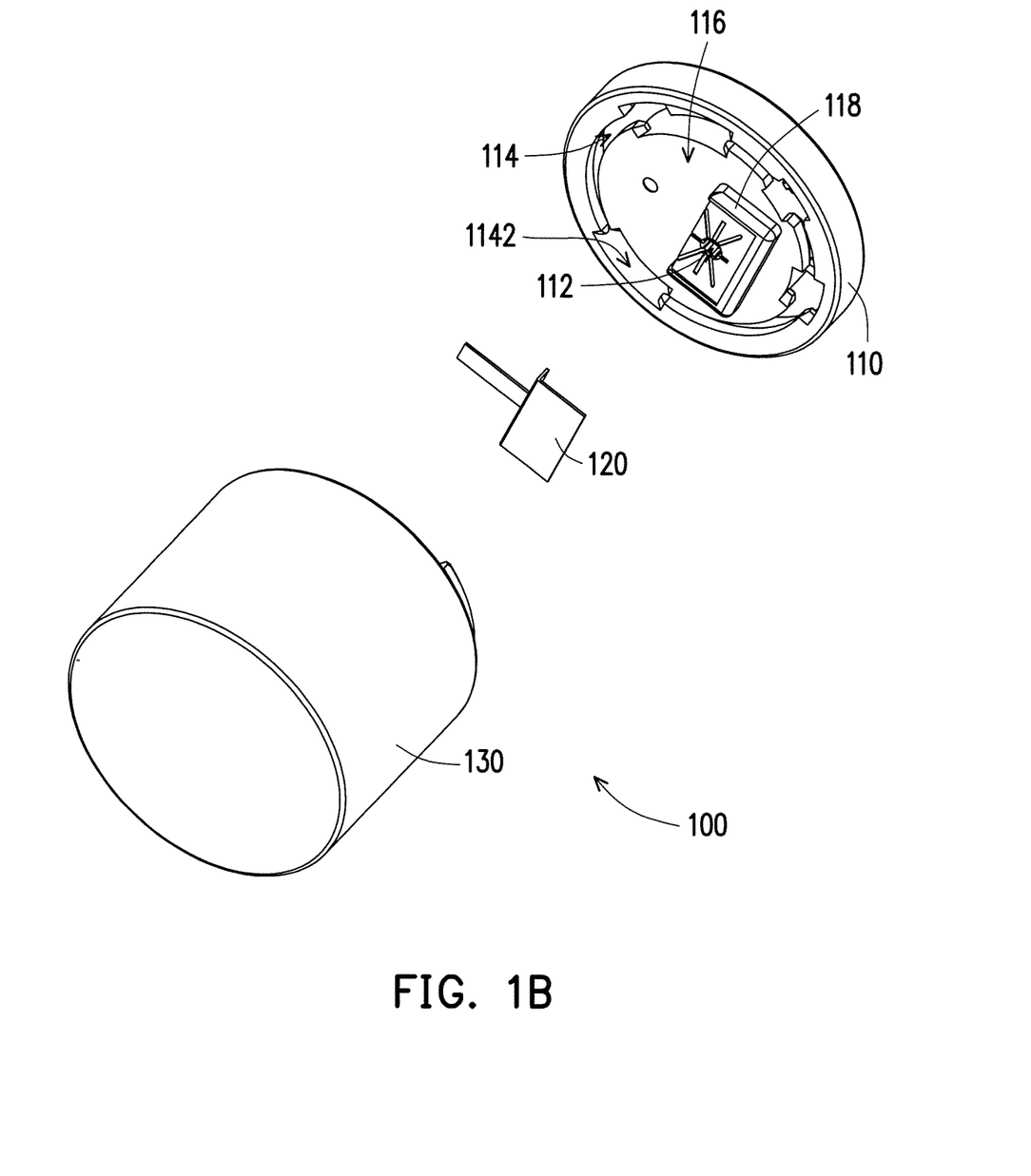
FIG. 1B shows a schematic three-dimensional exploded view of the blood plasma and blood cell separation device of FIG. 1A from another perspective.

FIG. 1A shows a schematic three-dimensional exploded view of a blood plasma and blood cell separation device 100 in an embodiment of the invention. FIG. 1B shows a schematic three-dimensional exploded view of the blood plasma and blood cell separation device 100 of FIG. 1A from another perspective. With reference to FIG. 1A and FIG. 1B, in this embodiment, the blood plasma and blood cell separation device 100 includes a first body 110, a blood plasma separation membrane 120 and a second body 130. The first body 110 is movably assembled to the second body 130 and has an injection port 112. The second body 130 has a collecting stage 132, and the collecting stage 132 has a collecting surface 133 and a sampling recess 134 on the collecting stage 132. The blood plasma separation membrane 120 is disposed on the first body 110 and may move along with the first body 110.

More specifically, in this embodiment, the first body 110 has a first surface 116 facing the second body 130. Herein, the first surface 116 is provided with a membrane carrier 118 protruding toward the second body 130, and the injection port 112 is disposed on the membrane carrier 118. The second body 130 has a second surface 131 facing the first body 110. Herein, the collecting stage 132 protrudes from the second surface 131 toward the first body 110. The sampling recess 134 is recessed from the collecting surface 133. The blood plasma separation membrane 120 is fixed on the membrane carrier 118 of the first body 110 and may face the collecting surface 133 of the collecting stage 132. When the blood plasma separation membrane 120 faces the collecting surface 133, a capillary action may be generated between the blood plasma separation membrane 120 and the collecting surface 133.

In this embodiment, the first body 110 has a first connecting portion 114, and the second body 130 has a second connecting portion 135 movably and detachably connected to the first connecting portion 114. In an embodiment, as shown in FIG. 1A and FIG. 1B, the first connecting portion 114 may be a sliding slot 114 that has a disengagement port 1142. The second connecting portion 135 may be a bump 135 that moves inside the sliding slot 114 and may move along the sliding slot 114 to the disengagement port 1142 to be detached from the sliding slot 114.

Figure 1C:
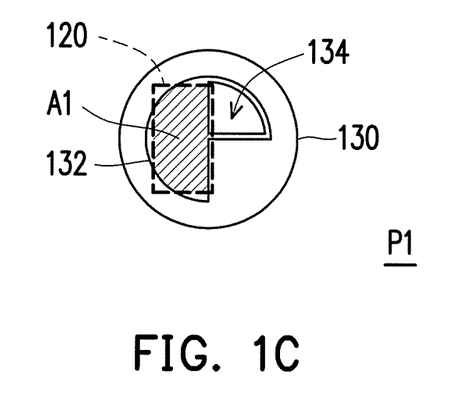
FIG. 1C shows a schematic top view of the blood plasma separation membrane and the collecting stage of FIG. 1A in a first relative position.
Figure 1D:
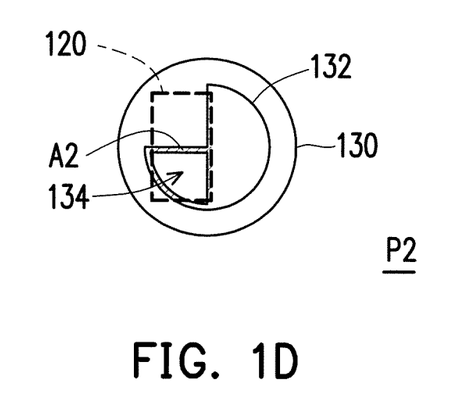
FIG. 1D shows a schematic top view of the blood plasma separation membrane and the collecting stage of FIG. 1A in a second relative position.

In this embodiment, the blood plasma separation membrane 120 is fixed on the first body 110. The first body 110 may carry the blood plasma separation membrane 120 to move relative to the second body 130 so as to make the blood plasma separation membrane 120 and the collecting stage 132 in a first relative position P1 and a second relative position P2 respectively.

FIG. 1C shows a schematic top view of the blood plasma separation membrane 120 and the collecting stage 132 of FIG. 1A in a first relative position P1. FIG. 1D shows a schematic top view of the blood plasma separation membrane 120 and the collecting stage 132 of FIG. 1A in a second relative position P2. In this embodiment, as shown in FIG. 1C, when the blood plasma separation membrane 120 and the collecting stage 132 are in the first relative position P1, the blood plasma separation membrane 120 and the collecting surface 133 has a first overlapping surface A1. As shown in FIG. 1D, when the blood plasma separation membrane 120 and the collecting stage 132 are in the second relative position P2, the blood plasma separation membrane 120 and the collecting surface 133 has a second overlapping surface A2. Herein, an area of the second overlapping surface A2 is smaller than an area of the first overlapping surface A1.

FIGS. 2A to 2D show schematic front views of a blood plasma and blood cell separating method in an embodiment of the invention. FIG. 3A and FIG. 3B show schematic views of blood plasma distribution when the blood plasma separation membrane 120 and the collecting stage 132 are in the first relative position P1 and in the second relative position P2 respectively. FIG. 3C shows a schematic top view of the second body 130 of the blood plasma and blood cell separation device 100 of FIG. 2D. First, with reference to FIG. 2A and FIG. 2B, when a blood 10 is injected from the injection port 112 of the first body 110, the blood 10 flows from the injection port 112 of the first body 110 to the blood plasma separation membrane 120 disposed on the first body 110. Herein, the blood 10 is, for example, whole blood, i.e. containing blood plasma, blood cells and platelets, and has a volume of 50 microliters (ul), for example.

Figure 2A:
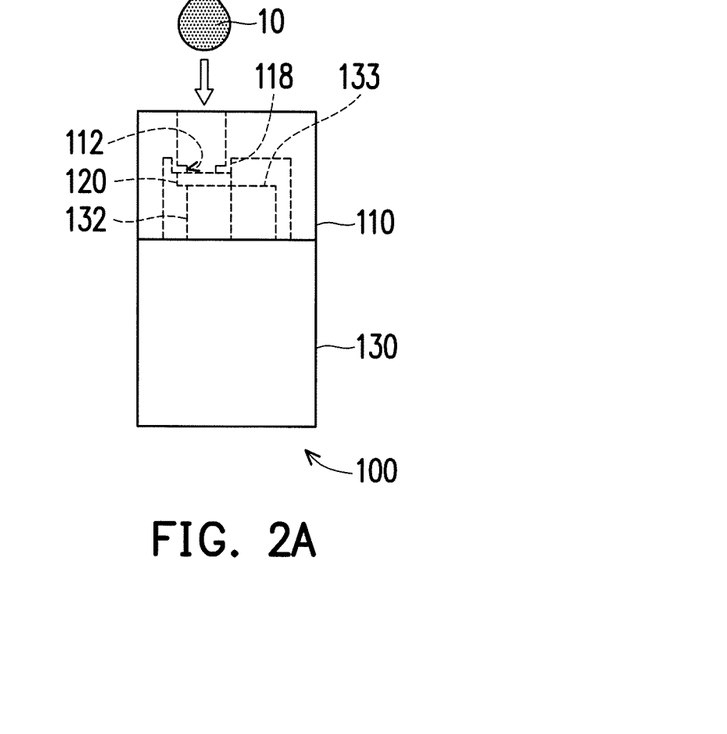
FIGS. 2A to 2D show schematic front views of a blood plasma and blood cell separating method in an embodiment of the invention.
Figure 2B:
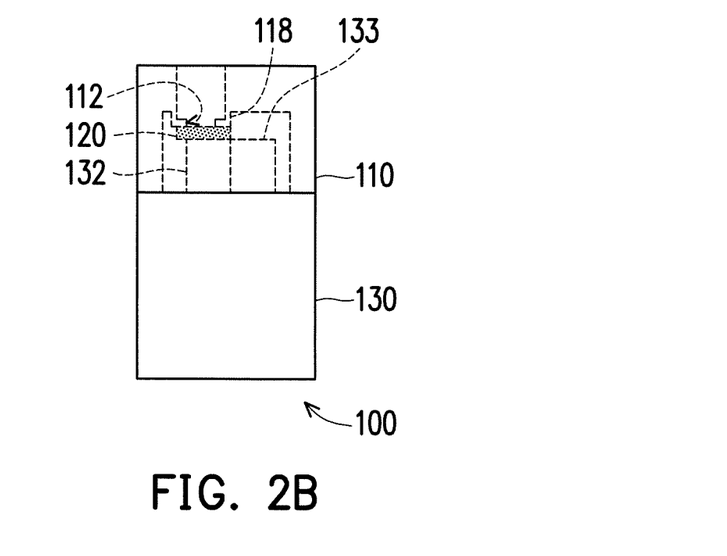
Figure 3A:
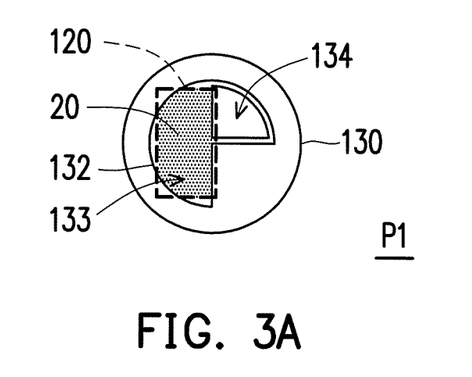
FIG. 3A shows a schematic view of blood plasma distribution when the blood plasma separation membrane and the collecting stage are in the first relative position.
Figure 3B:
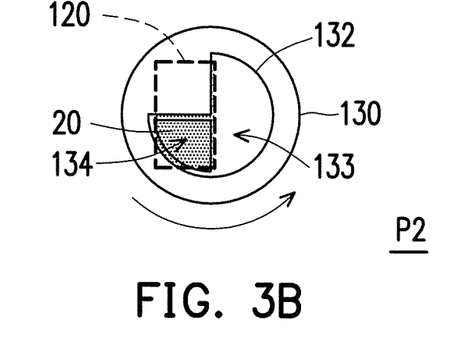
FIG. 3B shows a schematic view of blood plasma distribution when the blood plasma separation membrane and the collecting stage are in the second relative position.
Figure 3C:
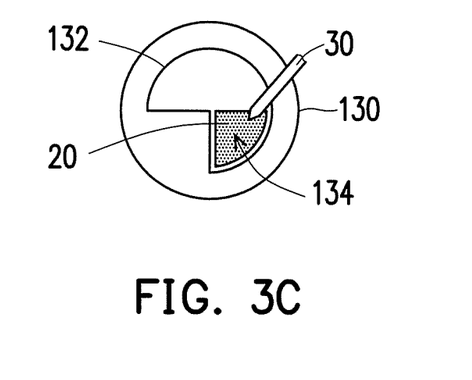
FIG. 3C shows a schematic top view of the second body of the blood plasma and blood cell separation device of FIG. 2D.

Then, with reference to FIG. 2B and FIG. 3A, an inlet side (i.e. the side closer to the injection port 112) of the blood separation membrane 120 has an aperture of about 100 micrometers, and an outlet side (i.e. the side closer to the collecting stage 132) of the blood separation membrane 120 has an aperture of about 1 micrometer. Consequently, when the blood 10 passes through the blood plasma separation membrane 120, red blood cells and platelets are blocked by the blood plasma separation membrane 120 to be unable to pass through the blood plasma separation membrane 120. In this way, only a blood plasma 20 may pass through the blood plasma separation membrane 120, thereby achieving the purpose of separating the blood plasma 20.

In this embodiment, when the blood 10 is injected from the injection port 112 of the first body 110, the blood plasma separation membrane 120 and the collecting stage 132 are in the first relative position P1. That is, the blood plasma membrane 120 faces the collecting surface 133, and the blood plasma membrane 120 and the collecting surface 133 has the first overlapping surface A1, as shown in FIG. 1C. A capillary force is generated between the collecting surface 133 of the collecting stage 132 and the blood plasma separation membrane 120 on the first overlapping surface A1 to attract the blood plasma 20 in the blood plasma separation membrane 120 so that the blood plasma 20 is separated from the blood plasma separation membrane 120. At this moment, as shown in FIG. 3A, the blood plasma 20 separated from the blood plasma separation membrane 120 is distributed on the first overlapping surface A1 of the collecting surface 133 of the collecting stage 132.

Figure 2C:
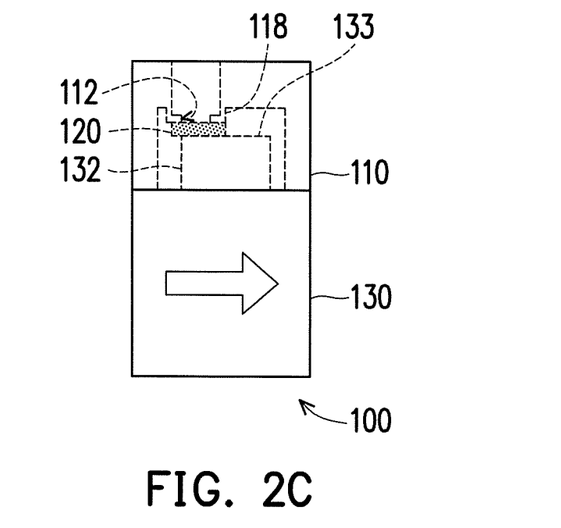

Then, with reference to FIG. 2C and FIG. 3B, by generating a relative movement, such as a relative rotation, between the first body 110 and the second body 130, the blood plasma 20 distributed on the first overlapping surface A1 of the collecting surface 133 enters in the sampling recess 134 on the collecting stage 132. Specifically, when the first body 110 is rotated relative to the second body 130, the area of the overlapping surface between the collecting surface 133 of the collecting stage 132 and the blood plasma separation membrane 120 becomes smaller, so that the area in which the blood plasma 20 may be distributed on the collecting surface 133 becomes smaller correspondingly and is unable to accommodate all of the blood plasma 20 separated from the blood plasma separation membrane 120. Consequently, the excess blood plasma 20 enters in the sampling recess 134 and is accommodated in the sampling recess 134. In other words, in this embodiment, the blood plasma 20 is accommodated in the sampling recess 134 of the second body 130 by the relative movement between the first body 110 and the second body 130. Of course, in other embodiments that are not shown, the type of the relative movement adopted by the first body and the second body may also be relative slide or other kind of motions, which still falls within the protected scope of this invention.

With reference to FIG. 1D and FIG. 3B, when the first body 110 carries the blood plasma separation membrane 120 to move relative to the second body 130 so that the blood plasma separation membrane 120 and the collecting stage 132 are in the second relative position P2, the blood plasma separation membrane 120 and the collecting surface 133 has the second overlapping surface A2. Because the second overlapping surface A2 is smaller than the first overlapping surface A1, the blood plasma 20 originally distributed on the first overlapping surface A1 may not be completely distributed on the second overlapping surface A2. Consequently, the excess blood plasma 20 enters in the sampling recess 134.

Figure 2D:
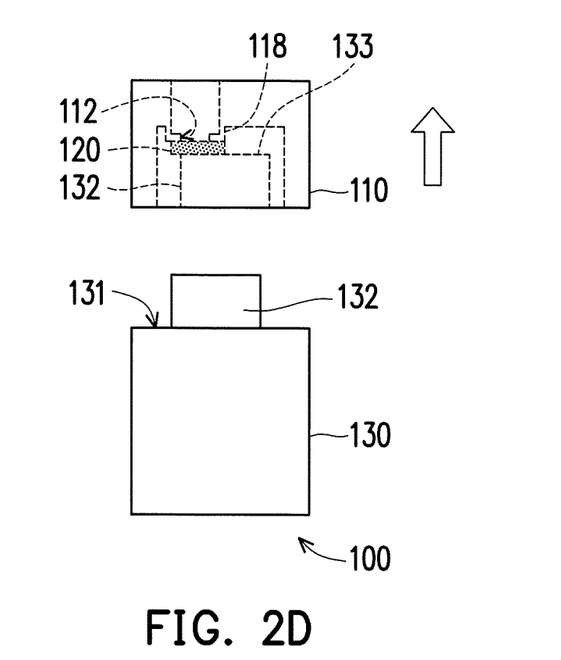

Finally, with reference to FIG. 2D and FIG. 3C, the first body 110 and the second body 130 are disassembled so as to separate the first body 110 and the second body 130. At this moment, a lancet 30 or a pipette (not shown) may be used to collect the blood plasma 20 in the sampling recess 134 of the second body 130.

In short, in the design of the blood plasma and blood cell separation device 100 of this embodiment, the first body 110 has the injection port 112 from which the blood 10 is injected and serves the function of fixing the blood plasma separation membrane 120, the blood plasma separation membrane 120 serves the function of separating the blood plasma 20 from the blood 10, and the second body 130 serves the function of removing the blood plasma 20 from the blood plasma separation membrane 120 and collecting the blood plasma 20. When the blood 10 enters the blood plasma separation membrane 120 from the injection port 112 of the first body 110, the blood plasma 20 in the blood plasma separation membrane 120 is separated by the capillary force between the collecting stage 132 of the second body 130 and the blood plasma separation membrane 120, and the blood plasma 20 enters in the sampling recess 134 by the relative movement between the first body 110 and the second body 130. In this way, after injecting the blood 10, a user simply needs to rotate and disassemble the first body 110 and the second body 130 to obtain the desired sample of the blood plasma 20.

In other words, for the blood plasma and blood cell separation device 100 of this embodiment, the step of applying a prior art absorbent material is not necessary. In this way, not only is the cost of the consumables reduced, the residual blood plasma is also reduced so as to improve the separation and utilization rate. The operation time is also reduced so that the desired sample of the blood plasma 20 may be obtained in an effective and speedy manner. Besides, the blood plasma and blood cell separating method using the blood plasma and blood cell separation device 100 of this embodiment allows the user to obtain the desired sample of the blood plasma 20 in a short time with only a small amount of whole blood.

In summary of the above, in the design of the blood plasma and blood cell separation device of the invention, the blood plasma in the blood plasma separation membrane is separated by a capillary force between the collecting stage of the second body and the blood plasma separation membrane, and the blood plasma enters in the sampling recess by the relative movement between the first body and the second body. In this way, after injecting the blood, the user simply needs to rotate and disassemble the first body and the second body to obtain the desired sample of the blood plasma. In other words, the blood plasma and blood cell separation device of the invention obtains the desired sample of the blood plasma in an effective and speedy manner, while the blood plasma and blood cell separating method using the blood plasma and blood cell separation device of the invention allows the user to obtain the desired sample of the blood plasma in a short time with only a small amount of whole blood.

Although the embodiments are already disclosed as above, these embodiments should not be construed as limitations on the scope of the invention. It will be apparent to those skilled in the art that various modifications and variations can be made to the disclosed embodiments without departing from the scope or spirit of this invention. In view of the foregoing, it is intended that the invention covers modifications and variations provided that they fall within the scope of the following claims and their equivalents.

What is claimed is:

1. A blood plasma and blood cell separation device, comprising:
   a first body having an injection port;
   a blood plasma separation membrane disposed on the first body; and
   a second body movably assembled to the first body and having a collecting stage, wherein the collecting stage has a collecting surface and a sampling recess on the collecting stage, wherein when a blood enters the blood plasma separation membrane from the injection port of the first body, a blood plasma in the blood plasma separation membrane is separated by a capillary force between the collecting stage of the second body and the blood plasma separation membrane, and the blood plasma enters in the sampling recess by a relative movement between the first body and the second body.

2. The blood plasma and blood cell separation device as recited in claim 1, wherein the first body has a first surface facing the second body, the first surface is provided with a membrane carrier protruding toward the second body, the injection port is disposed on the membrane carrier, and the blood plasma separation membrane is fixed on the membrane carrier.

3. The blood plasma and blood cell separation device as recited in claim 1, wherein when the blood plasma separation membrane and the collecting stage are in a first relative position, the blood plasma separation membrane and the collecting surface has a first overlapping surface, when the blood plasma separation membrane and the collecting stage are in a second relative position, the blood plasma separation membrane and the collecting surface has a second overlapping surface, and an area of the second overlapping surface is smaller than an area of the first overlapping surface.

4. The blood plasma and blood cell separation device as recited in claim 1, wherein the second body has a second surface facing the first body, the collecting stage protrudes from the second surface toward the first body, and the sampling recess is recessed from the collecting surface.

5. The blood plasma and blood cell separation device as recited in claim 1, wherein the first body has a first connecting portion, and the second body has a second connecting portion movably and detachably connected to the first connecting portion.

6. A blood plasma and blood cell separating method adapted for a blood plasma and blood cell separation device, the blood plasma and blood cell separation device comprising a first body having an injection port, a blood plasma separation membrane disposed on the first body, and a second body movably assembled to the first body and having a collecting stage, wherein the collecting stage has a collecting surface and a sampling recess on the collecting stage, the blood plasma and blood cell separating method comprising:
   injecting a blood into the injection port of the first body so that the blood plasma separation membrane absorbs the blood from the injection port, and separating a blood plasma in the blood plasma separation membrane by a capillary force between the collecting stage of the second body and the blood plasma separation membrane; and
   generating a relative movement between the first body and the second body so that the blood plasma enters in the sampling recess.

7. The blood plasma and blood cell separating method as recited in claim 6, wherein the first body has a first surface facing the second body, the first surface is provided with a membrane carrier protruding toward the second body, the injection port is disposed on the membrane carrier, and the blood plasma separation membrane is fixed on the membrane carrier.

8. The blood plasma and blood cell separating method as recited in claim 6, wherein when the blood plasma separation membrane and the collecting stage are in a first relative position, the blood plasma separation membrane and the collecting surface has a first overlapping surface, when the blood plasma separation membrane and the collecting stage are in a second relative position, the blood plasma separation membrane and the collecting surface has a second overlapping surface, and an area of the second overlapping surface is smaller than an area of the first overlapping surface.

9. The blood plasma and blood cell separating method as recited in claim 6, wherein the second body has a second surface facing the first body, the collecting stage protrudes from the second surface toward the first body, and the sampling recess is recessed from the collecting surface.

10. The blood plasma and blood cell separating method as recited in claim 6, wherein the first body has a first connecting portion, and the second body has a second connecting portion movably and detachably connected to the first connecting portion.

* * * * *